United States Patent [19]

Vitcak et al.

[11] Patent Number: 5,750,797
[45] Date of Patent: May 12, 1998

[54] PROCESS FOR THE PRODUCTION OF HYDROFLUOROETHERS

[75] Inventors: Daniel R. Vitcak, Cottage Grove; Richard M. Flynn, Mahtomedi, both of Minn.

[73] Assignee: Minnesota Mining and Manufacturing Company, St. Paul, Minn.

[21] Appl. No.: 632,697

[22] Filed: Apr. 15, 1996

[51] Int. Cl.$^6$ .................................................. C07C 41/00
[52] U.S. Cl. ........................................ 568/683; 568/681
[58] Field of Search ............................. 568/681, 683, 568/414

[56] References Cited

U.S. PATENT DOCUMENTS

| | | | |
|---|---|---|---|
| 2,519,983 | 8/1950 | Simons | 204/62 |
| 2,713,593 | 7/1955 | Brice et al. | 260/535 |
| 3,361,685 | 1/1968 | Pittman et al. | 260/2 |
| 3,504,000 | 3/1970 | Pittman et al. | 260/348 |
| 3,549,711 | 12/1970 | Merrill et al. | 260/614 |
| 3,897,502 | 7/1975 | Russell et al. | 260/614 F |
| 5,314,975 | 5/1994 | Badbirad et al. | |
| 5,352,785 | 10/1994 | Herzberg | |
| 5,360,582 | 11/1994 | Boyd et al. | |
| 5,466,877 | 11/1995 | Moore | |

FOREIGN PATENT DOCUMENTS

| | | | |
|---|---|---|---|
| 2287432 | 7/1976 | France | C07C 43/12 |
| 1 283 820 | 11/1968 | Germany | C07C 43/12 |
| P1283829.9-42 | 11/1968 | Germany | |
| 1 294 949 | 5/1969 | Germany | C07C 43/12 |
| 6-293686 | 10/1994 | Japan | C07C 43/12 |
| 8-34755 | 2/1996 | Japan | C07C 43/12 |
| 1193122 | 5/1970 | United Kingdom | C07C 43/02 |

OTHER PUBLICATIONS

Grant and Hackh's Chemical Dictionary, p. 119, 1987.
W. V. Childs et al., "Anodic Fluorination," *Organic Electrochemistry*, pp. 1103–1127, Marcel Dekker, Inc. (1991).
S. Nagase, "Electrochemical Fluorination," *Fluorine Chemistry Reviews*, pp. 77–106, Marcel Dekker, Inc. (1967).
T. Abe et al., "Electrochemical Fluorination (Simons Process) as a Route to Perfluorinated Organic Compounds of Industrial Interest," *Preparation, Properties, and Industrial Applications of Organofluorine Compounds*, pp. 19–43, John Wiley & Sons (1982).
S. Misaki et al., "Development of New Refrigerant," *International CFC and Halon Alternatives Conference*, pp. 114–120 (1994).
D. England, "Catalytic Conversion of Fluoralkyl Alkyl Ethers to Carbonyl Compounds," *Journal of Organic Chemistry*, pp. 4007–4008, vol. 49 (1984).
M. C. Sneed et al., "The Alkali Metals," *Comprehensive Inorganic Chemistry*, pp. 61–64, vol. 6, D. van Nostrand Company, Inc. (1957).
R. D. Smith et al., "The Chemistry of Carbobyl Fluoride," *Perfluoroisopropyl Ketones*, pp. 4285–4288, vol. 84 (Nov. 20, 1962).
P. Zurer, "Looming Ban on Production of CFC's Halons Spurs Switch to Substitutes," *Chemical & Engineering News*, pp. 12–18 (Nov. 15, 1993).
S. Yamashita, "Development of CFC Alternatives Containing Oxygen Atom," pp. 55–69, International Conference on CFC and BFC (Halons), Shanghai, China (Aug. 1994).
H. Kobler et al. "Eine einfache Synthese von Tetraalkylammoniumsalzen mit funktionellen Anionen," Liebigs Ann. Chem., pp. 1937–1945 (1978).

*Primary Examiner*—Gary Geist
*Assistant Examiner*—Karl J. Puttlitz, Jr.
*Attorney, Agent, or Firm*—John A. Burtis

[57] ABSTRACT

Briefly, in one aspect, this invention provides an improved alkylation process for the preparation of primary and secondary hydrofluoroether compounds, said process comprising:

(1) combining in a polar, aprotic solvent:
  a) a fluorinated carbonyl-containing compound;
  b) an anhydrous source of fluoride ion;
  c) a tertiary or aromatic amine; and
  d) optionally, an effective amount of a phase transfer catalyst;
(2) contacting the resulting mixture with an alkylating agent; and
(3) recovering hydrofluoroether from the resulting product mixture.

44 Claims, No Drawings

PROCESS FOR THE PRODUCTION OF HYDROFLUOROETHERS

FIELD OF THE INVENTION

This invention relates to the production of hydrofluoroethers. More particularly, the present invention relates to the production of hydrofluoroether compounds by the alkylation of certain fluorinated carbonyl-containing compounds.

BACKGROUND OF THE INVENTION

Chlorofluorocarbon compounds (CFCs) and hydrochlorofluorocarbon compounds (HCFCs) as a class possess unique chemical stability and solvent properties and have until only recently been used in a wide variety of applications, finding utility in drying processes, cleaning processes (e.g., the removal of flux residues from printed circuit boards), and vapor degreasing applications. While these materials were initially believed to be environmentally benign, they now are linked to ozone depletion. According to the Montreal Protocol and its attendant amendments, production and use of CFCs must be discontinued (see, e.g., P. S. Zurer, *Looming Ban on Production of CFCs, Halons Spurs Switch to Substitutes*, CHEM. & ENG'G NEWS, Nov. 15, 1993, at 12). Characteristics sought in CFC and HCFC replacements, in addition to low ozone depletion potential, typically include boiling point ranges that are suitable for a variety of solvent cleaning applications, low flammability, and low toxicity. Replacement solvents should also have the ability to dissolve both hydrocarbon-based and fluorocarbon-based soils.

A group of compounds spotlighted recently as promising substitutes for ozone-depleting solvents are hydrofluoroethers (HFEs). These compounds, as a class, are particularly promising candidates not only because of their zero ozone-depleting potential, but also because they exhibit superior solvent properties.

A number of synthetic routes to hydrofluoroethers are known. These methods may be broadly divided into two groups; methods of fluorinating an ether compound, and methods where the ether linkage is formed within a compound by reaction with a fluorine-containing compound. The former methods include: (1) Direct fluorination of an ether compound; and (2) Electrochemical fluorination of an ether compound. The latter methods include: (3) The addition reaction of an alcohol to a fluorinated olefin; (4) Alkylation of a partially fluorinated alcohol; and (5) Alkylation of an acid fluoride using a sulfonic acid ester as the alkylating agent. Japanese Patent No. JP 6-293686 provides a description of these varied methods.

Suitable methods for alkylation of acyl fluorides include those described by French Patent Publication No. 2,287,432 and German Patent Publication No. 1,294,949, and such useful alkylation processes typically comprise the reaction of a perfluorinated acyl fluoride or a perfluorinated ketone with an anhydrous source of fluoride ion (e.g., an alkali metal fluoride such as potassium fluoride, cesium fluoride, or silver fluoride) in an anhydrous polar, aprotic solvent to produce a perfluorinated alkoxide that is subsequently reacted with a suitable alkylating agent such as a dialkyl sulfate, an alkyl halide, or an alkyl perfluoroalkanesulfonate, to produce a primary or secondary hydrofluoroether.

While the alkylation processes described above may be commercially viable as they are practiced in the art, there is a continuing need to improve product yields and minimize the production of undesired byproduct. In the interests of optimizing the overall process, there is also an ever-present and strong interest in recovering and recycling back to the process any potentially available unused, unreacted, or otherwise recoverable process components.

SUMMARY OF THE INVENTION

Briefly, in one aspect, this invention provides an improved alkylation process for the preparation of hydrofluoroether compounds, said process comprising:

(1) combining in a polar, aprotic solvent:

a) a fluorinated carbonyl-containing compound of the formula:

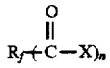

wherein n is 1 to 3; and when n is 1, $R_f$ is a fluorinated, preferably perfluorinated, alkyl group having from 1 to about 15 carbon atoms that may be substituted or unsubstituted, cyclic or acyclic, linear or branched and may optionally contain one or more catenary heteroatoms such as nitrogen, sulfur, or oxygen;

when n is 2, $R_f$ is a fluorinated, preferably perfluorinated, alkylene group having from 1 to about 15 carbon atoms that may be substituted or unsubstituted, cyclic or acyclic, linear or branched and may optionally contain one or more catenary heteroatoms such as nitrogen, sulfur, or oxygen;

when n is 3, $R_f$ is a fluorinated, preferably perfluorinated, alkylidene group having from 1 to about 15 carbon atoms that may be substituted or unsubstituted, cyclic or acyclic, linear or branched and may optionally contain one or more catenary heteroatoms such as nitrogen, sulfur, or oxygen; and wherein each X is independently a halogen atom or is of the formula $R'_f$ or $OOCR'_f$ where $R'_f$ is a fluorinated, preferably perfluorinated, alkyl group having from 1 to about 10 carbon atoms that may be substituted or unsubstituted, cyclic or acyclic, linear or branched and may optionally contain one or more catenary heteroatoms such as nitrogen, sulfur, or oxygen; where X is an $R'_f$ group, that $R'_f$ group may form a ring with the $R_f$ group previously defined such as would give, e.g., a cyclic ketone;

b) an anhydrous source of fluoride ion such as a metal fluoride (e.g., potassium fluoride or cesium fluoride), a metal bifluoride, or a quaternary ammonium or phosphonium fluoride;

c) an amount of a tertiary or aromatic amine sufficient to neutralize substantially all acid contaminants present in the reactant mixture; and d) optionally, an effective amount of a phase transfer catalyst selected from the group consisting of quaternary ammonium and phosphonium salts, crown ethers, and cryptands;

(2) contacting the resulting mixture with an alkylating agent of the general formula:

wherein:

R is a substituted or unsubstituted, cyclic or acyclic, linear or branched, non-fluorinated or partially fluorinated alkyl group having from 1 to about 10 carbon atoms that may optionally also contain one or more catenary heteroatoms such as oxygen, sulfur or nitrogen; and Y is a chlorine, bromine, or iodine atom or is a group of the formula $R'—SO_2—O—$ where R' is a phenyl or toluyl group or is a non-fluorinated or fully fluorinated alkyl group or an alkoxy group either of which may contain from 1 to about 10 carbon atoms; and (3) recovering hydrofluoroether from the resulting product mixture.

In another aspect the present invention provides a process for the production of secondary hydrofluoroethers according to the formula:

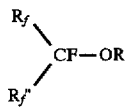

wherein:

$R_f$ is a fluorinated, preferably perfluorinated, alkyl group having from 1 to about 15 carbon atoms that may be substituted or unsubstituted, cyclic or acyclic, linear or branched and may optionally contain one or more catenary heteroatoms such as nitrogen, sulfur, or oxygen;

$R''_f$ is a perfluorinated, linear or branched alkyl group having from 2 to 6 carbon atoms or a perfluorinated cycloalkyl group having from 3 to 6 carbon atoms; and R is a substituted or unsubstituted, cyclic or acyclic, linear or branched, non-fluorinated or partially fluorinated alkyl group having from 1 to about 10 carbon atoms that may optionally also contain one or more catenary heteroatoms such as oxygen, sulfur or nitrogen;

said process comprising:

(1) combining in a polar, aprotic solvent:

a) a fluorinated carbonyl-containing compound of the formula:

wherein $R_f$ is as defined above and wherein X is a halogen atom or is $OOCR'_f$ where $R'_f$ is a fluorinated, preferably perfluorinated, alkyl group having from 1 to about 10 carbon atoms that may be substituted or unsubstituted, cyclic or acyclic, linear or branched and may optionally contain one or more catenary heteroatoms such as nitrogen, sulfur, or oxygen;

b) a perfluorinated olefin having from 2 to 6 carbon atoms;

c) an anhydrous source of fluoride ion such as a metal fluoride (e.g., potassium fluoride or cesium fluoride), a metal bifluoride, or a quaternary ammonium or phosphonium fluoride;

d) an amount of a tertiary or aromatic amine sufficient to neutralize substantially all acid contaminants present in the reactant mixture; and e) optionally, an effective amount of a phase transfer catalyst selected from the group consisting of quaternary ammonium and phosphonium salts, crown ethers, and cryptands;

(2) contacting the resulting mixture with an alkylating agent of the general formula:

wherein:

R is a substituted or unsubstituted, cyclic or acyclic, linear or branched, non-fluorinated or partially fluorinated alkyl group having from 1 to about 10 carbon atoms that may optionally also contain one or more catenary heteroatoms such as oxygen, sulfur or nitrogen; and Y is a chlorine, bromine, or iodine atom or is a group of the formula $R'—SO_2—O—$ where R' is a phenyl or toluyl group or is a non-fluorinated or fully fluorinated alkyl group or an alkoxy group either of which may contain from 1 to about 10 carbon atoms; and (3) recovering secondary hydrofluoroether from the resulting product mixture.

In yet another aspect, the present invention provides a method for recovering solvent from an alkylation process for the preparation of hydrofluoroether compounds comprising:

(1) combining in a glycol ether solvent:

a) a fluorinated carbonyl-containing compound of the formula:

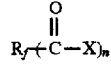

wherein n is 1 to 3; and when n is 1, $R_f$ is a fluorinated, preferably perfluorinated, alkyl group having from 1 to about 15 carbon atoms that may be substituted or unsubstituted, cyclic or acyclic, linear or branched and may optionally contain one or more catenary heteroatoms such as nitrogen, sulfur, or oxygen;

when n is 2, $R_f$ is a fluorinated, preferably perfluorinated, alkylene group having from 1 to about 15 carbon atoms that may be substituted or unsubstituted, cyclic or acyclic, linear or branched and may optionally contain one or more catenary heteroatoms such as nitrogen, sulfur, or oxygen;

when n is 3, $R_f$ is a fluorinated, preferably perfluorinated, alkylidene group having from 1 to about 15 carbon atoms that may be substituted or unsubstituted, cyclic or acyclic, linear or branched and may optionally contain one or more catenary heteroatoms such as nitrogen, sulfur, or oxygen; and wherein each X is independently a halogen atom or is of the formula $R'_f$ or $OOCR'_f$ where $R'_f$ is a fluorinated, preferably perfluorinated, alkyl group having from 1 to about 10 carbon atoms that may be substituted or unsubstituted, cyclic or acyclic, linear or branched and may optionally contain one or more catenary heteroatoms such as nitrogen, sulfur, or oxygen; where X is an $R'_f$ group, that $R'_f$ group may form a ring with the $R_f$ group previously defined such as would give, e.g., a cyclic ketone;

b) an anhydrous source of fluoride ion such as a metal fluoride (e.g., potassium fluoride or cesium fluoride), a metal bifluoride, or a quaternary ammonium or phosphonium fluoride;

c) an amount of a tertiary or aromatic amine sufficient to neutralize substantially all acid contaminants present in the reactant mixture; and d) optionally, an effective amount of a phase transfer catalyst selected from the group consisting of quaternary ammonium and phosphonium salts, crown ethers, and cryptands;

(2) contacting the mixture with a sulfonate or sulfate group-containing alkylating agent of the general formula:

wherein:

R is a substituted or unsubstituted, cyclic or acyclic, linear or branched, non-fluorinated or partially fluorinated alkyl group having from 1 to about 10 carbon atoms that may optionally also contain one or more catenary heteroatoms such as oxygen, sulfur or nitrogen; and Y is a group of the formula $R'—SO_2—O—$ where R' is a phenyl or toluyl group or is a non-fluorinated or fully fluorinated alkyl group or an alkoxy group either of which may contain from 1 to about 10 carbon atoms;

(3) contacting the resulting product mixture with an amount of potassium hydroxide sufficient to neutralize unreacted sulfate group-containing alkylating agent while maintaining the mixture at or below a temperature of 35° C. until said neutralization is substantially complete;

(4) contacting the neutralized product mixture with an amount of hydrogen fluoride sufficient to bring the mixture to a substantially neutral pH;

(5) recovering hydrofluoroether product from the product mixture; and (6) separately recovering the glycol ether solvent

DETAILED DESCRIPTION OF THE INVENTION

In accordance with one aspect of the present invention, it has been found that the perfluorinated acyl halides, acyl anhydrides, and ketones most useful as feed materials for a state-of-the-art alkylation process often are contaminated with acids (e.g., with HF) that have a deleterious effect on the kinetics of the alkylation reaction and on the yields of desired product. Small amounts of acid present in other process reagents, such as in the solvent, the anhydrous fluorine source, and the phase transfer catalyst, can also have a similar effect. Collectively, the acid present in these feed materials to the alkylation process will be referred to for the purpose of description as "acid contaminants," and it has been found that the addition of an effective amount of a tertiary or aromatic amine to the reactant mixture prior to alkylation alleviates the effects of these acid contaminants, maintaining high product yields and also desirable reaction kinetics. It will be understood, however, that a reduction of acid contaminant concentration, and not necessarily its elimination, will provide the benefits taught by the invention, and that therefore, in utilizing the process of this invention relatively small amounts of acid contaminant may be tolerated without adverse impact on process kinetics or product yields.

The hydrofluoroether compounds made in accordance with this invention may include those represented by the following general formula:

(I)

wherein x is 1 to 3; and when x is 1, $R_f$ is a fluorinated, preferably perfluorinated, alkyl group having from 1 to about 15 carbon atoms that may be substituted or unsubstituted, cyclic or acyclic, linear or branched and may optionally contain one or more catenary heteroatoms such as nitrogen, sulfur, or oxygen;

when x is 2, $R_f$ is a fluorinated, preferably perfluorinated, alkylene group having from 1 to about 15 carbon atoms that may be substituted or unsubstituted, cyclic or acyclic, linear or branched and may optionally contain one or more catenary heteroatoms such as nitrogen, sulfur, or oxygen;

when x is 3, $R_f$ is a fluorinated, preferably perfluorinated, alkylidene group having from 1 to about 15 carbon atoms that may be substituted or unsubstituted, cyclic or acyclic, linear or branched and may optionally contain one or more catenary heteroatoms such as nitrogen, sulfur, or oxygen; and wherein each R is independently selected as a substituted or unsubstituted, cyclic or acyclic, linear or branched, non-fluorinated or partially fluorinated alkyl group having from 1 to about 10 carbon atoms that may optionally also contain one or more catenary heteroatoms such as oxygen, sulfur or nitrogen.

Examples of compounds suitable for alkylation according to the invention include perfluorinated acyl halides, preferably perfluorinated acyl fluorides, perfluorinated acyl anhydrides, and perfluorinated ketones. Such compounds may be represented generally by the following formula:

(II)

wherein n is 1 to 3; and when n is 1, $R_f$ is a fluorinated, preferably perfluorinated, alkyl group having from 1 to about 15 carbon atoms that may be substituted or unsubstituted, cyclic or acyclic, linear or branched and may optionally contain one or more catenary heteroatoms such as nitrogen, sulfur, or oxygen;

when n is 2, $R_f$ is a fluorinated, preferably perfluorinated, alkylene group having from 1 to about 15 carbon atoms that may be substituted or unsubstituted, cyclic or acyclic, linear or branched and may optionally contain one or more catenary heteroatoms such as nitrogen, sulfur, or oxygen;

when n is 3, $R_f$ is a fluorinated, preferably perfluorinated, alkylidene group having from 1 to about 15 carbon atoms that may be substituted or unsubstituted, cyclic or acyclic, linear or branched and may optionally contain one or more catenary heteroatoms such as nitrogen, sulfur, or oxygen; and wherein each X is independently a halogen atom or is of the formula $R'_f$ or $OOCR'_f$ where $R'_f$ is a fluorinated, preferably perfluorinated, alkyl group having from 1 to about 10 carbon atoms that may be substituted or unsubstituted, cyclic or acyclic, linear or branched and may optionally contain one or more catenary heteroatoms such as nitrogen, sulfur, or oxygen; where X is an $R'_f$ group, that $R'_f$ group may form a ring with the $R_f$ group previously defined such as would give, e.g., a cyclic ketone;

The perfluorinated acyl halides can be prepared, for example, by electrochemical fluorination (ECF) of a corresponding hydrocarbon carboxylic acid, or derivative thereof such as a carboxylic acid halide, anhydride or ester, using either anhydrous hydrogen fluoride ("Simons" ECF) or KF.2HF ("Phillips" ECF) as an electrolyte. Details of the "Simons" ECF process may be found in U.S. Pat. No. 2,519,983 (Simons) and by S. Nagase in 1 FLUORINE CHEM. REV. 77, 77–106 (1967), and W. V. Childs et al., *Anodic Florination*, in ORGANIC FLUOROCHEMISTRY 1103–04, 1113–17 (Henning Lund & Manuel M. Baizer eds., 1991) provide a description of the "Phillips" ECF process.

Perfluorinated acyl halides and perfluorinated ketones can also be prepared by dissociation of perfluorinated carboxylic acid esters (which can be prepared from the corresponding hydrocarbon or partially-fluorinated carboxylic acid esters by direct fluorination with fluorine gas). Dissociation can be achieved by contacting the perfluorinated ester with a source of fluoride ion under reacting conditions (see the method described in U.S. Pat. No. 5,466,877 (Moore), whose description is incorporated herein by reference) or by combining the ester with at least one initiating reagent selected from the group consisting of: gaseous, non-hydroxylic nucleophiles; liquid, non-hydroxylic nucleophiles; and mixtures of at least one non-hydroxylic nucleophile (gaseous, liquid, or solid) and at least one solvent that is inert to acylating agents.

Initiating reagents that can be employed in this dissociation reaction are those gaseous or liquid, non-hydroxylic nucleophiles and mixtures of gaseous, liquid, or solid, non-hydroxylic nucleophile(s) and solvent (hereinafter termed "solvent mixtures") that are capable of nucleophilic reaction with perfluorinated esters. The presence of small amounts of hydroxylic nucleophiles can be tolerated. Suitable gaseous or liquid, non-hydroxylic nucleophiles include dialkylamines, trialkylamines, carboxamides, alkyl sulfoxides, amine oxides, oxazolidones, pyridines, and the like, and mixtures thereof. Suitable non-hydroxylic nucleophiles for use in solvent mixtures include such gaseous or liquid, non-hydroxylic nucleophiles, as well as solid, non-hydroxylic nucleophiles, e.g., fluoride, cyanide, cyanate, iodide, chloride, bromide, acetate, mercaptide, alkoxide, thiocyanate, azide, trimethylsilyl difluoride, bisulfite, and bifluoride anions, which can be utilized in the form of alkali metal, ammonium, alkyl-substituted ammonium (mono-, di-, tri-, or tetra-substituted), or quaternary phosphonium salts, as well as mixtures thereof. Such salts are in general commercially available but, if desired, can be prepared by known methods, e.g., those described by M. C. Sneed & R. C. Brasted, *The Alkali Metals*, in 6 COMPREHENSIVE INORGANIC CHEMISTRY 61–64 (1957) and by H. Kobler et al. in ANN. CHEM. 1937 (Justus Liebigs ed., 1978) whose descriptions are also incorporated herein by reference.

Useful anhydrous fluorine-containing compounds are those that will dissociate to form an anhydrous source of fluoride ion. Such compounds include metal fluorides (e.g., potassium fluoride, rubidium fluoride, and cesium fluoride), metal bifluorides, and quaternary ammonium and phosphonium fluorides. To ensure an adequate yield of desired product, the anhydrous fluorine-containing compound must be reacted with the fluorinated carbonyl-containing compound at least stoichiometrically, i.e., in a 1:1 molar ratio, relative to the carbonyl groups, —(CO)—X. Preferably, however, to favor maximum yield, the anhydrous fluorine-containing compound is reacted in a slight molar excess, up to about a ratio of 1.1:1 or 1.5:1.

Any tertiary or aromatic amine may be incorporated into the process of the present invention to improve yields of hydrofluoroether product by reducing the concentration of acid contaminants in the process feedstock. Examples of useful tertiary amines for this purpose include substituted and unsubstituted, cyclic or acyclic trialkyl amines, e.g., trimethyl amine, triethyl amine, trioctyl amine, tribenzyl amine, benzyl dimethyl amine, tetramethyl methylene diamine, N-methyl piperidine, N,N-dimethyl piperazine, and N-methyl morpholine; and aromatic amines such as pyridine, 2,6-dimethyl pyridine, 3,4-dimethyl pyridine, 3,5-dimethyl pyridine, 2-picoline, 3-picoline, 4-picoline and quinoline. To reduce the occurrence of undesired side reactions, preferred tertiary amines are those amines, such as tribenzyl amine, that do not contain an aliphatic β-hydrogen atom relative to the amino nitrogen atom. Those amines containing large substituent groups (e.g., tribenzyl amine) that cause the amine to exhibit some degree of steric hindrance are also preferred to reduced undesired side reactions. To serve its purpose, the tertiary or aromatic amine need only be added in "catalytic" (i.e., relatively small) amounts, preferably present in the reaction mixture in an amount at least stoichiometric to the amount of acid contaminant. Typically, the tertiary or aromatic amine will constitute between 0.01 mol % and 5.0 mol % of the total reactants employed for the alkylation reaction, preferably between 0.01 mol % and 1.0 mol %.

Those phase transfer catalysts that may optionally be employed in the alkylation reaction of the invention include quaternary ammonium salts, quaternary phosphonium salts (e.g. monoalkyl sulfate- and monoalkyl sulfonate salts), crown ethers, and cryptands. Preferred salt counter ions are those that are less reactive to an alkylating agent (i.e., less nucleophilic) than is a fluoride ion. Useful crown ethers include 4'-aminobenzyl-15-crown-5, 1-aza-12-crown-5, 1-aza-15-crown-5, 1-aza-18-crown-5, bis[(benzo-15-crown-5)-15-ylmethyl] pimelate, dicyclohexano-18-crown-6, 4'-formylbenzo-15-crown-5, 2-(hydroxymethyl)-15-crown-5, 4'-nitrobenzo-15-crown-5, and poly[(dibenzo-18-crown-6)-coformaldehyde]. Useful commercially available cryptands include Kryptofix™ 21, 211, 222, and 222b, all available from Aldrich Chemical Co. Because of their relative abundance and cost effectiveness, quaternary ammonium salts are preferred, and commercially available ammonium salts include Adogen™ 464, a methyltrialkyl($C_8$–$C_{10}$) ammonium chloride, from Aldrich Chem. Co. Another preferred phase-transfer catalyst is $(C_8H_{17})_3N^+CH_3^-$ $OSO_3CH_3$, the anion of which is particularly less reactive toward the alkylating agent. The inclusion of a phase transfer catalyst in the process of the invention is preferred, as its presence in the reaction mixture increases the overall rate of the alkylation reaction and increases the yield of desired hydrofluoroether product. If present, a phase transfer catalyst is typically added at a concentration constituting between about 0.001 mol % and about 5.0 mol % of the alkylation reaction mixture.

Any of the alkylating agents known and described in the art may be used in the present invention, including dialkyl sulfates (e.g., dimethyl sulfate, diethyl sulfate, and dipropyl sulfate), alkyl halides (e.g., methyl iodide, methyl chloride, methyl bromide, ethyl iodide, ethyl bromide and ethyl iodide), alkyl p-toluenesulfonates (e.g., methyl p-toluenesulfonate), alkyl perfluoroalkanesulfonates (e.g., methyl perfluoromethanesulfonate, 2,2,2-trifluoroethyl perfluorobutanesulfonate and methyl perfluorobutanesulfonate) and the like. Among the useful alkylating agents are those that may be represented by the formula:

$$Y—R \qquad \text{(III)}$$

wherein:

R is a substituted or unsubstituted, cyclic or acyclic, linear or branched, non-fluorinated or partially fluorinated alkyl group having from 1 to about 10 carbon atoms that may optionally also contain one or more catenary heteroatoms such as oxygen, sulfur or nitrogen; and Y is a chlorine, bromine, or iodine atom or is a group of the formula R'—$SO_2$—O— where R' is a phenyl or toluyl group or is a non-fluorinated or fully fluorinated alkyl group or an alkoxy group either of which may contain from 1 to about 10 carbon atoms.

The choice of a given alkylating agent will of course depend in large measure on the desired hydrofluoroether product; an alkyl substituent in the alkylating agent will determine one side of the ether linkage. Thus, for example, if 1-methoxy nonafluoroisobutane is a desired ether product, an alkylating agent having a methyl substituent (such as methyl triflate) must be used. To ensure an adequate yield of desired product, the alkylating agent must be reacted with the fluorinated carbonyl-containing compound at least stoichiometrically, i.e., in a 1:1 molar ratio. Preferably, however, to favor maximum yield, the alkylating agent is reacted in a slight molar excess, up to about a ratio of 1.1:1 or 1.5:1.

The solvent or solvents employed as the process medium for the process of the invention must be inert to the reactants under the conditions of the alkylation reaction. Suitable solvents include polar, aprotic solvents such as glycol ether solvents (e.g., glyme, diglyme, triglyme, and tetraglyme), tetrahydrofuran, acetonitrile, and dimethylformamide. The product ether, i.e., one according to Formula I presented supra, may also be employed as the carrier solvent for the invention. Commercially available glycol ether solvents include Proglyme™ DDM available Dow Chemical Co. Because glycol either solvents may be nearly fully recovered from the products and byproducts of the alkylation reaction through the use of a preferred post-reaction recovery process, the use of a glycol ether solvent is preferred in the practice of the invention.

The alkylation process of the invention may be performed in any suitable reaction vessel, although when volatile reagents are used, or when volatile products are produced, a pressure vessel is preferred. The process may be carried out by adding the fluorinated carbonyl-containing compound, the anhydrous fluorine source, the tertiary amine, solvent and, if employed, the phase transfer catalyst to the reactor with moderate agitation at a temperature between approximately −60° C. and 30° C., preferably between about −30° C. and about 30° C. These reagents may be added to the reactor in any order. To minimize the occurrence of undesired side reactions, however, the alkylating agent is preferably the last material to be combined with the others.

Upon addition of all reagents to the reaction vessel, the mixture may be reacted at a temperature between about 30° C. and about 130° C., preferably between 40° C. and 80° C., and held at an elevated temperature until completion of the reaction, typically for approximately 10 hours, at which time the hydrofluoroether product may be recovered from the product mixture using any suitable separation process. Where the alkylating agent employed for the reaction is toxic (e.g., dimethyl sulfate), however, the hydrofluoroether product preferably is recovered after neutralization of excess alkylating agent with potassium hydroxide, sodium hydroxide, ammonium hydroxide, or any other suitable base such as a tertiary amine, and after the addition of water to dissolve byproduct salts and other water-soluble byproducts. It will be understood that in carrying out the alkylation process as described herein, mixtures of hydrofluoroethers according to the general Formula I will be produced, including multiple isomers of a particular hydrofluoroether.

In a second embodiment, the present invention provides a process for the production of secondary hydrofluoroethers of the formula:

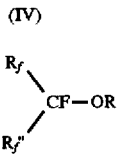

(IV)

wherein:

R$_f$ is a fluorinated, preferably perfluorinated, alkyl group having from 1 to about 15 carbon atoms that may be substituted or unsubstituted, cyclic acyclic, linear or branched and may optionally contain one or more catenary heteroatoms such as nitrogen, sulfur, or oxygen;

R"$_f$ is a perfluorinated alkyl group having from 2 to 6 carbon atoms or a perfluorinated cycloalkyl group having from 3 to 6 carbon atoms; and R is a substituted or unsubstituted, cyclic or acyclic, linear or branched, non-fluorinated or partially fluorinated alkyl group having from 1 to about 10 carbon atoms that may optionally also contain one or more catenary heteroatoms such as oxygen, sulfur or nitrogen.

The process is carried out in a manner identical to alkylation process described supra by reacting a fluorinated, preferably perfluorinated, acyl halide of the general formula:

(V)

wherein R$_f$ is as defined above for Formula IV and wherein X is a halogen atom or is OOCR'$_f$ where R'$_f$ is a fluorinated, preferably perfluorinated, alkyl group having from 1 to about 10 carbon atoms that may be substituted or unsubstituted, cyclic or acyclic, linear or branched and may optionally contain one or more catenary heteroatoms such as nitrogen, sulfur, or oxygen;

with a perfluorinated olefin having from 2 to 6 carbon atoms, preferably hexafluoropropene, and reacting the two with an anhydrous source of fluoride ion, a tertiary amine, an alkylating agent, and optionally also a phase transfer catalyst in a polar, aprotic solvent. The reactants may be reacted in the proportions and in the manner previously described. It will again be understood that in carrying out this embodiment, mixtures of the desired secondary ether product, including multiple isomers of a particular product ether, may be produced.

A highly preferred embodiment of the alkylation processes of this invention involves the use of a glycol ether solvent and a sulfate group-containing alkylating agent and provides a method of nearly complete recovery of the glycol ether solvent, a high-cost component of the overall process. In practice of this embodiment, the reaction mixture, containing a glycol ether or glycol ether mixture, is charged with sufficient aqueous potassium hydroxide to quench unreacted alkylating agent following the alkylation reaction, and water is added to dissolve water-soluble byproducts. The mixture is held at a temperature below 35° C. for a period of time sufficient to allow complete neutralization of the alkylating agent (measurable, for example, when the pH of the mixture rises to at least 13), typically for at least 30 minutes and up to several hours. Excess potassium hydroxide is then neutralized by the addition of hydrogen fluoride (either anhydrous or aqueous in any useful concentration) to a pH of between 7 and 8 to produce a mixture from which the hydrofluoroether product can be removed; HF being the preferred acid to use for this purpose because potassium fluoride (the salt formed from its reaction with excess KOH) is highly soluble in water. It is important in carrying out the neutralization that the product solution be kept at a temperature below 35° C. until completely neutralized to avoid further reaction of the potassium alkyl sulfate to give potassium sulfate that will impede the recovery of the solvent.

To recover the hydrofluoroether product from the glycol ether solution following neutralization, the solution may be distilled (fractionally or otherwise) at an elevated temperature, recovering the primary hydrofluoroether product and low boiling byproducts overhead by condensation. The residual solution will phase split, separating into a bottom aqueous salt phase and a top phase rich in glycol ether solvent. The glycol ether phase may then be dried by vacuum fractionation, separating the phase into dry glycol ether and a glycol ether/water azeotrope. The recovered dry glycol ether will contain less than 100 ppm water, a concentration reusable in the alkylation process without adverse effect on molar yield or purity of the resulting hydrofluoroether product, and it will also contain any excess phase transfer catalyst where a phase transfer catalyst was employed in the alkylation reaction from which it is recovered. The recovered "wet" glycol/water azeotrope can be recycled to the vacuum fractionation feed, i.e., the glycol ether-rich phase of the phase split, to recover further amounts of glycol ether solvent. Recovery of glycol ether solvent herein described can return more than 98% of initial solvent.

The following examples are offered to aid in a better understanding of the present invention. This list is not to be construed as an exhaustive compilation of embodiments of the processes taught by this invention and the examples are not to be unnecessarily construed as limiting the scope thereof.

EXAMPLES
Preparation of Heptafluoroisobutyryl Fluorides

Heptafluoroisobutyryl fluoride, the precursor to 1-methoxy nonafluoroisobutane, was prepared by electrochemical fluorination of isobutyric anhydride (in the presence of 3 wt. % dimethyl disulfide) in a Simons ECF cell of the type described in U.S. Pat. No. 2,713,593 (Brice et al.) and in R. E. BANKS, PREPARATION, PROPERTIES AND INDUSTRIAL APPLICATIONS OF ORGANOFLUORINE COMPOUNDS 19–43 (1982).

The gaseous products from the cell were further purified by distillation. The product phase yielded a mixture of about 56 wt % heptafluoroisobutyryl fluoride, 24 wt % heptafluoro-n-butyryl fluoride and 20 wt % perfluorinated, inert cyclic ethers. This mixture could be used in subsequent alkylations without further purification. As used herein, the term "perfluorobutyryl fluoride" will refer to the mixture of heptafluoroisobutyryl fluoride and heptafluoro-n-butyryl fluoride just described.

Preparation of 1-Methoxynonafluoroisobutane

Example 1

A 600 mL stainless steel Parr pressure reactor was charged with spray-dried potassium fluoride (1.10 mole equivalents relative to perfluorobutyryl fluoride), anhydrous diglyme (1.0 weight equivalents relative to perfluorobutyryl fluoride), Adogen™ 464 (0.013 mole equivalents relative to perfluorobutyryl fluoride, purified by dissolving in diglyme, followed by fractional distillation to remove isopropanol) and benzyldimethylamine (0.13 mole equivalents relative to perfluorobutyryl fluoride). The vessel was sealed, cooled with dry ice, charged with perfluorobutyryl fluoride to which 5000 ppm of hydrogen fluoride had been added (to determine the effect of HF contamination of the acyl fluoride), then allowed to warm to room temperature with stirring. Dimethyl sulfate (1.42 mole equivalents relative to perfluorobutyryl fluoride) was then charged to the reactor under pressure and the reactor held at 25° C. for one hour then heated to 40° C. for an additional ten hours.

The reactor was then charged with aqueous potassium hydroxide (100 g at a concentration of 22.5 wt %) to neutralize any unreacted dimethyl sulfate and stirred for 30 minutes at 30° C. until the solution pH was greater than 13. Excess aqueous HF (48 wt % concentration) was added to the solution until the pH was 7–8, and the product 1-methoxy nonafluoroisobutane fraction was distilled from the reaction mixture. The distillate was washed with water to remove small amounts of methanol, then fractionally distilled to further purify the desired product. B.P. 60° C., Yield 90%.

Examples 2–21 and Comparative Examples C1–C6

1-Methoxy nonafluoroisobutane was prepared using the procedure of Example 1, but varying the stoichiometry of one or more of the reagents, or the reaction temperature. The stoichiometry, reaction conditions, and yields are summarized in Table 1. For the comparative examples, C1–C6, no tertiary or aromatic amine was added, and other reactants and reaction conditions were varied as shown below in Table 1. The yields obtained from these reactions are also summarized by Table 1.

In Examples 2–4, and in Comparative Examples C1–C2, all shown in Table 1, the perfluorobutyryl fluoride contained 5000 ppm of added hydrogen fluoride to determine the effect of a acyl fluoride contaminated by HF. In Examples 19–20 and in Comparative Examples C5–C6, the feed material was contaminated by the addition of water to generate 250 ppm H⁺, again to determine the effect of an acyl fluoride contaminated by HF. In all other Examples, no acid or water contaminants were added.

TABLE 1

| Example | KF (mole eq.) | Diglyme (wt. eq.) | Dimethyl Sulfate (mole eq.) | Adogen™ 464 (mole eq.) | Amine (mole eq.) | Temperature/ Time | Yield |
|---|---|---|---|---|---|---|---|
| 1 | 1.10 | 1.00 | 1.42 | 0.013 | benzyldimethyl amine (0.13) | 1 hr @ 25° C. 10 hrs @ 40° C. | 90% |
| C1 | 1.10 | 1.00 | 1.42 | — | — | 1 hr @ 25° C. 12 hrs @ 40° C. | 72% |
| 2 | 1.10 | 1.02 | 1.42 | 0.013 | triethylamine (0.12) | 1 hr @ 25° C. 10 hrs @ 40° C. | 90% |
| 3 | 1.12 | 1.00 | 1.45 | — | benzyldimethyl amine (0.12) | 1 hr @ 25° C. 10 hrs @ 40° C. | 83% |
| C2 | 1.10 | 1.00 | 1.42 | 0.013 | — | 1 hr @ 25° C. 10 hrs @ 40° C. | 86% |
| 4 | 1.10 | 1.00 | 1.42 | 0.013 | benzyldimethyl amine (0.13) | 1 hr @ 25° C. 10 hrs @ 40° C. | 90% |
| 5 | 1.20 | 1.0 | 1.40 | 0.013 | benzyldimethyl amine (0.02) | 1 hr @ 25° C. 12 hrs @ 40° C. | 88% |
| 6 | 1.08 | 1.7 | 1.18 | 0.005 | triethylamine (0.03) | 18 hrs @ 25° C. | 88% |
| 7 | 1.34 | 1.9 | 1.34 | 0.011 | tetramethylethylene diamine (0.07) | 1 hr @ 30° C. 12 hrs @ 60° C. | 88% |
| 8 | 1.13 | 1.0 | 1.32 | — | triethylamine (0.03) | 1 hr @ 25° C. 12 hrs @ 40° C. | 89% |
| 9 | 1.05 | 0.95 | 1.24 | — | triethylamine | 1 hr @ 25° C. | 93% |

TABLE 1-continued

| Example | KF (mole eq.) | Diglyme (wt. eq.) | Dimethyl Sulfate (mole eq.) | Adogen™ 464 (mole eq.) | Amine (mole eq.) | Temperature/Time | Yield |
|---|---|---|---|---|---|---|---|
| 10 | 1.11 | 1.0 | 1.11 | — | triethylamine (0.03) | 12 hrs @ 40° C. 2 hrs @ 30° C. 12 hrs @ 40° C. | 85% |
| 11 | 1.03 | 0.95 | 1.04 | — | triethylamine (0.03) | 4 hrs @ 2° C. 12 hrs @ 25° C. | 86% |
| 12 | 1.00 | 0.90 | 1.50 | — | triethylamine (0.03) | 1 hr @ 25° C. 12 hrs @ 35° C. | 86% |
| 13 | 1.05 | 0.96 | 1.30 | — | trimethylamine (0.05) | 1 hr @ 30° C. 12 hrs @ 60° C. | 86% |
| 14 | 1.12 | 2.08 | 1.21 | 0.012 | triethylamine (0.12) | 1 hr @ 25° C. 12 hrs @ 40° C. | 83% |
| 15 | 1.10 | 1.00 | 1.30 | 0.050 | benzyldimethyl amine (0.045) | 2 hrs @ 25° C. 2 hrs @ 40° C. | 89% |
| 16 | 1.17 | 1.07 | 1.38 | 0.012 | tribenzylamine (0.045) | 1 hr @ 25° C. 12 hrs @ 40° C. | 93% |
| C3 | 1.06 | 0.96 | 1.25 | — | — | 1 hr @ 25° C. 12 hrs @ 40° C. | 67% |
| 17 | 1.13 | 1.00 | 1.32 | — | triethylamine (0.03) | 1 hr @ 25° C. 12 hrs @ 40° C. | 89% |
| C4 | 1.06 | 0.96 | 1.26 | 0.013 | — | 1 hr @ 25° C. 12 hrs @ 40° C. | 83% |
| 18 | 1.17 | 1.07 | 1.38 | 0.012 | tribenzylamine (0.045) | 1 hr @ 25° C. 12 hrs @ 40° C. | 93% |
| C5 | 1.10 | 1.00 | 1.10 | — | — | 1 hr @ 25° C. 12 hrs @ 40° C. | 65% |
| C6 | 1.10 | 1.00 | 1.10 | 0.013 | — | 1 hr @ 25° C. 12 hrs @ 40° C. | 76% |
| 19 | 1.10 | 1.00 | 1.10 | — | tribenzylamine (0.193) | 1 hr @ 25° C. 12 hrs @ 40° C. | 71% |
| 20 | 1.10 | 1.00 | 1.10 | 0.013 | tribenzylamine (0.193) | 1 hr @ 25° C. 12 hrs @ 40° C. | 75% |
| 21 | 1.10 | 1.00 | 1.30 | 0.013 | pyridine (0.030) | 1 hr @ 25° C. 10 hrs @ 40° C. | 93% |

As shown by the data of Table 1, the inclusion of a tertiary or aromatic amine to the alkylation process in accordance with the present invention increases product yield above that obtained using an alkylation under similar conditions without a tertiary or aromatic amine. As is further demonstrated by the data, the addition of a phase transfer catalyst to the alkylation process further increases product yield above that obtained without its use.

Example 22

The starting material, perfluoro-(2-methyl-pentan-3-one), was prepared by fluoride catalyzed addition of perfluoropropionyl fluoride to hexafluoropropylene according to the procedure described in R. D. Smith et al., 84 J. AM. CHEM. SOC. 4285 (1962).

Using essentially the procedure of Example 1, a 1-L flask, equipped with an addition funnel an overhead stirrer, nitrogen inlet, and condensor was charged with spray-dried potassium fluoride (43.0 g, 0.74 mole), anhydrous diglyme (373 g), Adogen™ 464 (10 g of 71% solution, 0.015 mole, prepared by dissolving Adogen™ 464 in diglyme, followed by fractional distillation to remove isopropanol) and tribenzylamine (7.37 g, 0.025 mole). Perfluoro-(2-methyl-pentan-3-one) ($C_2F_5COCF(CF_3)_2$, 180.6 g, 0.571 mole) was added dropwise with vigorous stirring under a nitrogen atmosphere to exclude moisture. Following complete addition of the ketone, dimethyl sulfate (93.4 g, 0.74 mole) was added dropwise and the reaction mixture stirred at room temperature overnight.

Aqueous potassium hydroxide was then added dropwise and vigorously stirred overnight. Water was added and the product ether azeotropically distilled. The lower product ether phase was collected, washed with brine to yield 185 g of $(C_2F_5CF(OCH_3)CF(CF_3)_2$, 95% pure by GLC. This crude product was further purified by distillation, b.p. 90°–92° C.

Example 23

Using essentially the procedure of Example 1, a 1-L flask, equipped with an addition funnel, nitrogen inlet and condensor was charged with spray-dried potassium fluoride (47 g, 0.81 mole), anhydrous diglyme (332 g), Adogen™ 464 (10.2 g of 71% solution, 0.016 mole) and tribenzylamine (8.05 g, 0.028 mole). Perfluoro-3-methyl-butan-2-one $(CF_3COCF(CF_3)_2$, 166 g of 95% purity: 0.592 mole), made in accordance with the method described in R. D. Smith et al., 84 J. AM. CHEM. SOC. 4285 (1962), was added dropwise with vigorous stirring under a nitrogen atmosphere to exclude moisture. Following complete addition of the ketone, diethyl sulfate (125 g, 0.81 mole) was added dropwise and the reaction mixture stirred at room temperature for 64 hours.

Aqueous potassium hydroxide (170 g of 50% aqueous solution) was then added dropwise and vigorously stirred for 45 minutes, followed by an additional 18 g of solid KOH and 100 ml of water. The product ether was then azeotropically distilled. The lower product ether phase was collected, washed with brine to yield 179.2 g of $CF_3CF(OCH_2CH_3)CF(CF_3)_2$, 93.2% pure by GLC. This crude product was further purified by distillation, b.p. 90° C. The product structure was confirmed by IR and $^{19}F$ NMR.

Example 24

Preparation of $C_3F_7CF(OCH_3)CF(CF_3)_2$

A clean, dry 600 mL stainless steel pressure vessel was charged with spray-dried potassium fluoride (34.9 g, 0.60 mole) and anhydrous diglyme (183 g), sealed and cooled with dry ice. Perfluoroisobutyryl fluoride (161 g of 66.4% purity, 0.49 mole) and hexafluoropropene (75 g, 0.50 moles) were added to the cooled vessel through an inlet. The vessel was then heated to 70° C., held at his temperature for five hours, then cooled to 25° C.

A mixture of tribenzylamine (4.3 g, 0.015 moles), methyl trioctylammonium methyl sulfate ($CH_3(C_8H_{17})_3N^+ CH_3OSO_3^-$, 5.9 g of a 53% solution in diglyme, 0.0065 mole) and diglyme (50 g) were transferred to the vessel from a second pressure vessel through an inlet. The vessel was maintained at 40° C. for 16 hours, then at 60° C. for two hours, then cooled to 25° C. Aqueous potassium hydroxide (100 g of 22.5 wt % solution, 0.40 moles) was added to the reactor through the inlet and heated to 35° C. for 30 minutes.

Excess pressure was vented from the reactor and the contents transferred to a 1 L flask equipped with a stirrer, thermometer, Barret trap and dry ice condensor. Aqueous hydrogen fluoride was added to the reaction mixture until the pH was 7–8. The crude product was isolated by distillation under reduced pressure, then the distillate washed with an equal volume of water to yield 233.4 grams of product (59.2% purity, 80.6% yield based on perfluorobutyryl fluoride). The product was confirmed by GC/MS and $^{19}F$ NMR.

We claim:

1. An alkylation process for the preparation of hydrofluoroether compounds, said process comprising:

(1) combining in a polar, aprotic solvent:
  a) a fluorinated carbonyl-containing compound of the formula:

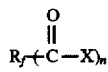

wherein n is 1 to 3; and
  when n is 1, $R_f$ is a fluorinated alkyl group having from 1 to about 15 carbon atoms that may be substituted or unsubstituted, cyclic or acyclic, linear or branched and may contain one or more catenary heteroatoms;
  when n is 2, $R_f$ is a fluorinated alkylene group having from 1 to about 15 carbon atoms that may be substituted or unsubstituted, cyclic or acyclic, linear or branched and may contain one or more catenary heteroatoms;
  when n is 3, $R_f$ is a fluorinated alkylidene group having from 1 to about 15 carbon atoms that may be substituted or unsubstituted, cyclic or acyclic, linear or branched and may contain one or more catenary heteroatoms; and
  wherein each X is independently a halogen atom or is of the formula $R'_f$ or $OOCR'_f$ where $R'_f$ is a fluorinated alkyl group having from 1 to about 10 carbon atoms that may be substituted or unsubstituted, cyclic or acyclic, linear or branched and may contain one or more catenary heteroatoms; where X is an $R'_f$ group, that $R'_f$ group may form a ring with said $R_f$ group;
  b) an anhydrous source of fluoride ion; and
  c) an amount of a tertiary or aromatic amine sufficient to neutralize substantially all acid contaminants present in the reactant mixture;

(2) contacting the resulting mixture with an alkylating agent of the general formula:

Y—R wherein:
  R is a substituted or unsubstituted, cyclic or acyclic, linear or branched, non-fluorinated or partially fluorinated alkyl group having from 1 to about 10 carbon atoms that may contain one or more catenary heteroatoms; and
  Y is a chlorine, bromine, or iodine atom or is a group of the formula R'—$SO_2$—O— where R' is a phenyl or toluyl group or is a non-fluorinated or fully fluorinated alkyl group or an alkoxy group either of which may contain from 1 to about 10 carbon atoms; and (3) recovering hydrofluoroether from the resulting product mixture.

2. The process of claim 1 wherein the anhydrous source of fluoride ion is selected from the group consisting of metal fluorides, metal bifluorides, quaternary ammonium fluoride, and quaternary phosphonium fluoride and wherein the polar, aprotic solvent is selected from the group consisting of glycol ethers, tetrahydrofuran, acetonitrile, and dimethylformamide.

3. The process of claim 1 wherein the alkylating agent is selected from the group consisting of dialkyl sulfates, alkyl halides, alkyl-p-toluenesulfonates, partially fluorinated alkyl perfluoroalkanesulfonates and alkyl perfluoroalkanesulfonates.

4. The process of claim 1 wherein the tertiary or aromatic amine is selected from the group consisting of substituted and unsubstituted, cyclic and acyclic trialkyl amines, pyridine, 2,6-dimethyl pyridine, 3,4-dimethyl pyridine, 3,5-dimethyl pyridine, 2-picoline, 3-picoline, 4-picoline and quinoline.

5. The process of claim 1 wherein the tertiary or aromatic amine is added in amount equal to the molar concentration of the acid contaminants present in the reaction mixture.

6. The process of claim 1 wherein the tertiary or aromatic amine is present in the reactant mixture at a molar concentration of between 0.01 and 5.0 percent.

7. The process of claim 1 wherein the fluorinated carbonyl-containing compound is of the formula:

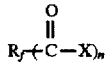

wherein n is 1 to 3; and
  when n is 1, $R_f$ is a perfluorinated alkyl group having from 1 to about 15 carbon atoms that may be substituted or unsubstituted, cyclic or acyclic, linear or branched and may contain one or more catenary heteroatoms;
  when n is 2, $R_f$ is a perfluorinated alkylene group having from 1 to about 15 carbon atoms that may be substituted or unsubstituted, cyclic or acyclic, linear or branched and may contain one or more catenary heteroatoms;
  when n is 3, $R_f$ is a perfluorinated alkylidene group having from 1 to about 15 carbon atoms that may be substituted or unsubstituted, cyclic or acyclic, linear or branched and may contain one or more catenary heteroatoms; and
  wherein each X is independently a halogen atom or is of the formula $R'_f$ or $OOCR'_f$ where $R'_f$ is a perfluorinated alkyl group having from 1 to about 10 carbon atoms that may be substituted or unsubstituted, cyclic or acyclic, linear or branched and may contain one or more catenary heteroatoms; where X is an $R'_f$ group, that $R'_f$ group may form a ring with said $R_f$ group.

8. An alkylation process for the preparation of hydrofluoroether compounds, said process comprising:
(1) combining in a polar, aprotic solvent:
a) a fluorinated carbonyl-containing compound of the formula:

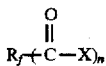

wherein n is 1 to 3; and
when n is 1, $R_f$ is a fluorinated alkyl group having from 1 to about 15 carbon atoms that may be substituted or unsubstituted, cyclic or acyclic, linear or branched and may contain one or more catenary heteroatoms;
when n is 2, $R_f$ is a fluorinated alkylene group having from 1 to about 15 carbon atoms that may be substituted or unsubstituted, cyclic or acyclic, linear or branched and may contain one or more catenary heteroatoms;
when n is 3, $R_f$ is a fluorinated alkylidene group having from 1 to about 15 carbon atoms that may be substituted or unsubstituted, cyclic or acyclic, linear or branched and may contain one or more catenary heteroatoms; and
wherein each X is independently a halogen atom or is of the formula $R'_f$ or $OOCR'_f$ where $R'_f$ is a fluorinated alkyl group having from 1 to about 10 carbon atoms that may be substituted or unsubstituted, cyclic or acyclic, linear or branched and may contain one or more catenary heteroatoms; where X is an $R'_f$ group, that $R'_f$ group may form a ring with said $R_f$ group;
b) an anhydrous source of fluoride ion;
c) an amount of a tertiary or aromatic amine sufficient to neutralize substantially all acid contaminants present in the reaction mixture; and
d) an effective amount of a phase transfer catalyst selected from the group consisting of quaternary ammonium and phosphonium salts, crown ethers, and cryptands;
(2) contacting the resulting mixture with an alkylating agent of the general formula:

Y—R wherein:
R is a substituted or unsubstituted, cyclic or acyclic, linear or branched, non-fluorinated or partially fluorinated alkyl group having from 1 to about 10 carbon atoms that may contain one or more catenary heteroatoms; and
Y is a chlorine, bromine, or iodine atom or is a group of the formula $R'—SO_2—O—$ where $R'$ is a phenyl or toluyl group or is a non-fluorinated or fully fluorinated alkyl group or an alkoxy group either of which may contain from 1 to about 10 carbon atoms; and
(3) recovering hydrofluoroether from the resulting product mixture.

9. The process of claim 8 wherein the anhydrous source of fluoride ion is selected from the group consisting of metal fluorides, metal bifluorides, quaternary ammonium fluorides, and quaternary phosphonium fluorides and wherein the polar, aprotic solvent is selected from the group consisting of glycol ethers, tetrahydrofuran, acetonitrile, and dimethylformamide.

10. The process of claim 8 wherein the alkylating agent is selected from the group consisting of dialkyl sulfates, alkyl halides, alkyl-p-toluenesulfonates, partially fluorinated alkyl perfluoroalkanesulfonates, and alkyl perfluoroalkanesulfonates.

11. The process of claim 8 wherein the tertiary or aromatic amine is selected from the group consisting of substituted and unsubstituted, cyclic and acyclic trialkyl amines, pyridine, 2,6-dimethyl pyridine, 3,4-dimethyl pyridine, 3,5-dimethyl pyridine, 2-picoline, 3-picoline, 4-picoline and quinoline.

12. The process of claim 8 wherein the tertiary or aromatic amine is added in amount equal to the molar concentration of the acid contaminants present in the reaction mixture.

13. The process of claim 8 wherein the tertiary or aromatic amine is present in the reactant mixture at a molar concentration of between 0.01 and 5.0 percent.

14. The process of claim 8 wherein the phase transfer catalyst is present in the reaction mixture at a molar concentration of between 0.001 and 5.0 percent.

15. The process of claim 8 wherein the fluorinated carbonyl-containing compound is of the formula:

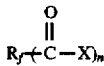

wherein n is 1 to 3; and
when n is 1, $R_f$ is a perfluorinated alkyl group having from 1 to about 15 carbon atoms that may be substituted or unsubstituted, cyclic or acyclic, linear or branched and may contain one or more catenary heteroatoms;
when n is 2, $R_f$ is a perfluorinated alkylene group having from 1 to about 15 carbon atoms that may be substituted or unsubstituted, cyclic or acyclic, linear or branched and may contain one or more catenary heteroatoms;
when n is 3, $R_f$ is a perfluorinated alkylidene group having from 1 to about 15 carbon atoms that may be substituted or unsubstituted, cyclic or acyclic, linear or branched and may contain one or more catenary heteroatoms; and
wherein each X is independently a halogen atom or is of the formula $R'_f$ or $OOCR'_f$ where $R'_f$ is a perfluorinated alkyl group having from 1 to about 10 carbon atoms that may be substituted or unsubstituted, cyclic or acyclic, linear or branched and may contain one or more catenary heteroatoms; where X is an $R'_f$ group, that $R'_f$ group may form a ring with said $R_f$ group.

16. A process for the production of a secondary hydrofluoroether comprising:
(1) combining in a polar, aprotic solvent:
a) a fluorinated carbonyl-containing compound of the formula:

wherein:
$R_f$ is a fluorinated alkyl group having from 1 to about 15 carbon atoms that may be substituted or unsubstituted, cyclic or acyclic, linear or branched and may optionally contain one or more catenary heteroatoms; and
X is a halogen atom or is $OOCR'_f$ where $R'_f$ is a fluorinated alkyl group having from 1 to about 10 carbon atoms that may be substituted or unsubstituted, cyclic or acyclic, linear or branched and may optionally contain one or more catenary heteroatoms;

b) a perfluorinated olefin having from 2 to 6 carbon atoms;

c) an anhydrous source of fluoride ion; and d) an amount of a tertiary or aromatic amine sufficient to neutralize substantially all acid contaminants present in the reaction mixture;

(2) contacting the resulting mixture with an alkylating agent of the general formula:

Y—R wherein:

R is a substituted or unsubstituted, cyclic or acyclic, linear or branched, non-fluorinated or partially fluorinated alkyl group having from 1 to about 10 carbon atoms that may contain one or more catenary heteroatoms; and Y is a chlorine, bromine, or iodine atom or is a group of the formula R'—SO$_2$—O— where R' is a phenyl or toluyl group or is a non-fluorinated or fully fluorinated alkyl group or an alkoxy group either of which may contain from 1 to about 10 carbon atoms; and (3) recovering hydrofluoroether from the resulting product mixture.

17. The process of claim 16 wherein the anhydrous source of fluoride ion is selected from the group consisting of metal fluorides, metal bifluorides, quaternary ammonium fluorides, and quaternary phosphonium fluorides and wherein the polar, aprotic solvent is selected from the group consisting of glycol ethers, tetrahydrofuran, acetonitrile, and dimethylformamide.

18. The process of claim 16 wherein the alkylating agent is selected from the group consisting of dialkyl sulfates, alkyl halides, alkyl-p-toluenesulfonates, partially fluorinated alkyl perfluoroalkanesulfonates, and alkyl perfluoroalkanesulfonates.

19. The process of claim 16 wherein the tertiary or aromatic amine is selected from the group consisting of substituted and unsubstituted, cyclic and acyclic trialkyl amines, pyridine, 2,6-dimethyl pyridine, 3,4-dimethyl pyridine, 3,5-dimethyl pyridine, 2-picoline, 3-picoline, 4-picoline and quinoline.

20. The process of claim 16 wherein the tertiary or aromatic amine is added in amount equal to the molar concentration of the acid contaminants present in the reaction mixture.

21. The process of claim 16 wherein the tertiary or aromatic amine is present in the reactant mixture at a molar concentration of between 0.01 and 5.0 percent.

22. A process for the production of a secondary hydrofluoroether comprising:

(1) combining in a polar, aprotic solvent:
   a) a fluorinated carbonyl-containing compound of the formula:

wherein:

R$_f$ is a fluorinated alkyl group having from 1 to about 15 carbon atoms that may be substituted or unsubstituted, cyclic or acyclic, linear or branched and may optionally contain one or more catenary heteroatoms; and X is a halogen atom or is OOCR'$_f$ where R'$_f$ is a fluorinated alkyl group having from 1 to about 10 carbon atoms that may be substituted or unsubstituted, cyclic or acyclic, linear or branched and may optionally contain one or more catenary heteroatoms;

b) a perfluorinated olefin having from 2 to 6 carbon atoms;

c) an anhydrous source of fluoride ion;

d) an amount of a tertiary or aromatic amine sufficient to neutralize substantially all acid contaminants present in the reaction mixture; and e) an effective amount of a phase transfer catalyst selected from the group consisting of quaternary ammonium and phosphonium salts, crown ethers, and cryptands;

(2) contacting the resulting mixture with an alkylating agent of the general formula:

Y—R wherein:

R is a substituted or unsubstituted, cyclic or acyclic, linear or branched, non-fluorinated or partially fluorinated alkyl group having from 1 to about 10 carbon atoms that may contain one or more catenary heteroatoms; and Y is a chlorine, bromine, or iodine atom or is a group of the formula R'—SO$_2$—O— where R' is a phenyl or toluyl group or is a non-fluorinated or fully fluorinated alkyl group or an alkoxy group either of which may contain from 1 to about 10 carbon atoms; and (3) recovering hydrofluoroether from the resulting product mixture.

23. The process of claim 22 wherein the anhydrous source of fluoride ion is selected from the group consisting of metal fluorides, metal bifluorides, quaternary ammonium fluorides, and quaternary phosphonium fluorides and wherein the polar, aprotic solvent is selected from the group consisting of glycol ethers, tetrahydrofuran, acetonitrile, and dimethylformamide.

24. The process of claim 22 wherein the alkylating agent is selected from the group consisting of dialkyl sulfates, alkyl halides, alkyl-p-toluenesulfonates, partially fluorinated alkyl perfluoroalkanesulfonates, and alkyl perfluoroalkanesulfonates.

25. The process of claim 22 wherein the tertiary or aromatic amine is selected from the group consisting of substituted and unsubstituted, cyclic and acyclic trialkyl amines, pyridine, 2,6-dimethyl pyridine, 3,4-dimethyl pyridine, 3,5-dimethyl pyridine, 2-picoline, 3-picoline, 4-picoline and quinoline.

26. The process of claim 22 wherein the tertiary or aromatic amine is added in amount equal to the molar concentration of the acid contaminants present in the reaction mixture.

27. The process of claim 22 wherein the tertiary or aromatic amine is present in the reactant mixture at a molar concentration of between 0.01 and 5.0 percent.

28. The process of claim 22 wherein the phase transfer catalyst is present in the reaction mixture at a molar concentration of between 0.001 and 5.0 percent.

29. A method for recovering solvent from an alkylation process for the preparation of hydrofluoroether compounds comprising:

(1) combining in a glycol ether solvent:
   a) a fluorinated carbonyl-containing compound of the formula:

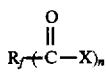

wherein n is 1 to 3; and when n is 1, $R_f$ is a fluorinated alkyl group having from 1 to about 15 carbon atoms that may be substituted or unsubstituted, cyclic or acyclic, linear or branched and may contain one or more catenary heteroatoms;

when n is 2, $R_f$ is a fluorinated alkylene group having from 1 to about 15 carbon atoms that may be substituted or unsubstituted, cyclic or acyclic, linear or branched and may contain one or more catenary heteroatoms;

when n is 3, $R_f$ is a fluorinated alkylidene group having from 1 to about 15 carbon atoms that may be substituted or unsubstituted, cyclic or acyclic, linear or branched and may contain one or more catenary heteroatoms; and wherein each X is independently a halogen atom or is of the formula $R'_f$ or $OOCR'_f$ where $R'_f$ is a fluorinated alkyl group having from 1 to about 10 carbon atoms that may be substituted or unsubstituted, cyclic or acyclic, linear or branched and may contain one or more catenary heteroatoms; where X is an $R'_f$ group, that $R'_f$ group may form a ring with said $R_f$ group;

b) an anhydrous source of fluoride ion;

c) an amount of a tertiary or aromatic amine sufficient to neutralize substantially all acid contaminants present in the reaction mixture;

(2) contacting the mixture with a sulfate group-containing alkylating agent of the general formula:

Y—R wherein:

R is a substituted or unsubstituted, cyclic or acyclic, linear or branched, non-fluorinated or partially fluorinated alkyl group having from 1 to about 10 carbon atoms that may contain one or more catenary heteroatoms; and Y is a group of the formula $R'$—$SO_2$—$O$— where $R'$ is a phenyl or toluyl group or is a non-fluorinated or fully fluorinated alkyl group or an alkoxy group either of which may contain from 1 to about 10 carbon atoms;

(3) contacting the resulting product mixture with an amount of potassium hydroxide sufficient to neutralize any unreacted sulfate group-containing alkylating agent while maintaining the mixture at or below a temperature of 35° C. until said neutralization is substantially complete;

(4) contacting the neutralized product mixture with an amount of hydrogen fluoride sufficient to bring the mixture to a substantially neutral pH; and (5) recovering hydrofluoroether product from the product mixture.

30. The process of claim 29 wherein the anhydrous source of fluoride ion is selected from the group consisting of metal fluorides, metal bifluorides, quaternary ammonium fluorides, and quaternary phosphonium fluorides.

31. The process of claim 29 wherein the alkylating agent is selected from the group consisting of dialkyl sulfates, alkyl-p-toluenesulfonates, and alkyl perfluoroalkanesulfonates.

32. The process of claim 29 wherein the tertiary or aromatic amine is selected from the group consisting of substituted and unsubstituted, cyclic and acyclic trialkyl amines, pyridine, 2,6-dimethyl pyridine, 3,4-dimethyl pyridine, 3,5-dimethyl pyridine, 2-picoline, 3-picoline, 4-picoline and quinoline.

33. The process of claim 29 wherein the tertiary or aromatic amine is added in amount equal to the molar concentration of the acid contaminants present in the reaction mixture.

34. The process of claim 29 wherein the tertiary or aromatic amine is present in the reactant mixture at a molar concentration of between 0.01 and 5.0 percent.

35. The process of claim 29 wherein the fluorinated carbonyl-containing compound is of the formula:

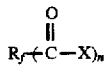

wherein n is 1 to 3; and when n is 1, $R_f$ is a perfluorinated alkyl group having from 1 to about 15 carbon atoms that may be substituted or unsubstituted, cyclic or acyclic, linear or branched and may contain one or more catenary heteroatoms;

when n is 2, $R_f$ is a perfluorinated alkylene group having from 1 to about 15 carbon atoms that may be substituted or unsubstituted, cyclic or acyclic, linear or branched and may contain one or more catenary heteroatoms;

when n is 3, $R_f$ is a perfluorinated alkylidene group having from 1 to about 15 carbon atoms that may be substituted or unsubstituted, cyclic or acyclic, linear or branched and may contain one or more catenary heteroatoms; and wherein each X is independently a halogen atom or is of the formula $R'_f$ or $OOCR'_f$ where $R'_f$ is a perfluorinated alkyl group having from 1 to about 10 carbon atoms that may be substituted or unsubstituted, cyclic or acyclic, linear or branched and may contain one or more catenary heteroatoms; where X is an $R'_f$ group, that $R'_f$ group may form a ring with said $R_f$ group.

36. A method for recovering solvent from an alkylation process for the preparation of hydrofluoroether compounds comprising:

(1) combining in a glycol ether solvent:

a) a fluorinated carbonyl-containing compound of the formula:

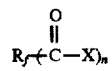

wherein n is 1 to 3; and when n is 1, $R_f$ is a fluorinated alkyl group having from 1 to about 15 carbon atoms that may be substituted or unsubstituted, cyclic or acyclic, linear or branched and may contain one or more catenary heteroatoms;

when n is 2, $R_f$ is a fluorinated alkylene group having from 1 to about 15 carbon atoms that may be substituted or unsubstituted, cyclic or acyclic, linear or branched and may contain one or more catenary heteroatoms;

when n is 3, $R_f$ is a fluorinated alkylidene group having from 1 to about 15 carbon atoms that may be substituted or unsubstituted, cyclic or acyclic, linear or branched and may contain one or more catenary heteroatoms; and wherein each X is independently a halogen atom or is of the formula $R'_f$ or $OOCR'_f$ where $R'_f$ is a fluorinated alkyl group having from 1 to about 10 carbon atoms that may be substituted or unsubstituted, cyclic or acyclic, linear or branched and may contain one or more catenary heteroatoms; where X is an $R'_f$ group, that $R'_f$ group may form a ring with said $R_f$ group;

b) an anhydrous source of fluoride ion;

c) an amount of a tertiary or aromatic amine sufficient to neutralize substantially all acid contaminants present in the reaction mixture; and d) an effective amount of a phase transfer catalyst selected from the group consisting of quaternary ammonium and phosphonium salts, crown ethers, and cryptands;

(2) contacting the mixture with a sulfate group-containing alkylating agent of the general formula:

$$Y-R$$

wherein:

R is a substituted or unsubstituted, cyclic or acyclic, linear or branched, non-fluorinated or partially fluorinated alkyl group having from 1 to about 10 carbon atoms that may contain one or more catenary heteroatoms; and Y is a group of the formula $R'-SO_2-O-$ where $R'$ is a phenyl or toluyl group or is a non-fluorinated or fully fluorinated alkyl group or an alkoxy group either of which may contain from 1 to about 10 carbon atoms;

(3) contacting the resulting product mixture with an amount of potassium hydroxide sufficient to neutralize any unreacted sulfate group-containing alkylating agent while maintaining the mixture at or below a temperature of 35° C. until said neutralization is substantially complete;

(4) contacting the neutralized product mixture with an amount of hydrogen fluoride sufficient to bring the mixture to a substantially neutral pH; and (5) recovering hydrofluoroether product from the product mixture.

37. The process of claim 36 wherein the anhydrous source of fluoride ion is selected from the group consisting of metal fluorides, metal bifluorides, quaternary ammonium fluorides, and quaternary phosphonium fluorides.

38. The process of claim 36 wherein the alkylating agent is selected from the group consisting of dialkyl sulfates, alkyl-p-toluenesulfonates, and alkyl perfluoroalkanesulfonates.

39. The process of claim 36 wherein the tertiary or aromatic amine is selected from the group consisting of substituted and unsubstituted, cyclic and acyclic trialkyl amines, pyridine, 2,6-dimethyl pyridine, 3,4-dimethyl pyridine, 3,5-dimethyl pyridine, 2-picoline, 3-picoline, 4-picoline and quinoline.

40. The process of claim 36 wherein the tertiary or aromatic amine is added in amount equal to the molar concentration of the acid contaminants present in the reaction mixture.

41. The process of claim 36 wherein the tertiary or aromatic amine is present in the reactant mixture at a molar concentration of between 0.01 and 5.0 percent.

42. The process of claim 36 wherein the phase transfer catalyst is present in the reaction mixture at a molar concentration of between 0.001 and 5.0 percent.

43. The process of claim 36 wherein the fluorinated carbonyl-containing compound is of the formula:

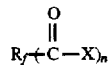

wherein n is 1 to 3; and when n is 1, $R_f$ is a perfluorinated alkyl group having from 1 to about 15 carbon atoms that may be substituted or unsubstituted, cyclic or acyclic, linear or branched and may contain one or more catenary heteroatoms;

when n is 2, $R_f$ is a perfluorinated alkylene group having from 1 to about 15 carbon atoms that may be substituted or unsubstituted, cyclic or acyclic, linear or branched and may contain one or more catenary heteroatoms;

when n is 3, $R_f$ is a perfluorinated alkylidene group having from 1 to about 15 carbon atoms that may be substituted or unsubstituted, cyclic or acyclic, linear or branched and may contain one or more catenary heteroatoms; and wherein each X is independently a halogen atom or is of the formula $R'_f$ or $OOCR'_f$ where $R'_f$ is a perfluorinated alkyl group having from 1 to about 10 carbon atoms that may be substituted or unsubstituted, cyclic or acyclic, linear or branched and may contain one or more catenary heteroatoms; where X is an $R'_f$ group, that $R'_f$ group may form a ring with said $R_f$ group.

44. An alkylation process for the preparation of hydrofluoroether compounds, said process comprising:

(1) combining in a polar, aprotic solvent:
a) perfluorinated carboxylic acid ester;
b) an anhydrous source of fluoride ion; and
c) an amount of a tertiary or aromatic amine sufficient to neutralize substantially all acid contaminants present in the reactant mixture;

(2) contacting the resulting mixture with an alkylating agent of the general formula:

$$Y-R$$

wherein:

R is a substituted or unsubstituted, cyclic or acyclic, linear or branched, non-fluorinated or partially fluorinated alkyl group having from 1 to about 10 carbon atoms that may contain one or more catenary heteroatoms; and Y is a chlorine, bromine, or iodine atom or is a group of the formula $R'-SO_2-O-$ where $R'$ is a phenyl or toluyl group or is a non-fluorinated or fully fluorinated alkyl group or an alkoxy group either of which may contain from 1 to about 10 carbon atoms; and (3) recovering hydrofluoroether from the resulting product mixture.

* * * * *